(12) United States Patent
Luo (10) Patent No.: US 11,279,737 B2
(45) Date of Patent: Mar. 22, 2022

(54) ANTIMICROBIAL PEPTIDE VARIANTS AND USES THEREOF

(71) Applicant: ANTINBIO, INC., Worcester, MA (US)

(72) Inventor: Ke Luo, Holden, MA (US)

(73) Assignee: ANTINBIO, INC., Worcester, MA (US)

(*) Notice: Subject to any disclaimer, the term of this patent is extended or adjusted under 35 U.S.C. 154(b) by 0 days.

(21) Appl. No.: 17/072,968

(22) Filed: Oct. 16, 2020

(65) Prior Publication Data

US 2021/0122791 A1    Apr. 29, 2021

Related U.S. Application Data (60) Provisional application No. 62/925,485, filed on Oct. 24, 2019.

(51) Int. Cl.
| | | |
|---|---|---|
| C07K 14/37 | (2006.01) | |
| A23L 33/18 | (2016.01) | |
| A61P 31/04 | (2006.01) | |
| A61K 8/64 | (2006.01) | |
| A61K 38/00 | (2006.01) | |

(52) U.S. Cl.
CPC ............. *C07K 14/37* (2013.01); *A23L 33/18* (2016.08); *A61K 8/64* (2013.01); *A61P 31/04* (2018.01); *A61K 38/00* (2013.01)

(58) Field of Classification Search
None
See application file for complete search history.

(56) References Cited

U.S. PATENT DOCUMENTS

2009/0227506 A1    9/2009    Hogenhaug et al.

FOREIGN PATENT DOCUMENTS

| CN | 104250293 A | 12/2014 |
| CN | 107857803 A | 3/2018 |
| CN | 111320678 A | 6/2020 |

OTHER PUBLICATIONS

GenBank entry PGH13380 (2017).*

* cited by examiner

*Primary Examiner* — Fred H Reynolds
(74) *Attorney, Agent, or Firm* — Nolan IP Law; Jason M. Nolan (57) ABSTRACT

An antimicrobial peptide variant having an amino acid sequence selected from SEQ ID NOs: 2-30 is provided. The antimicrobial peptide variant can have antimicrobial activity against *Bacillus subtilis, Staphylococcus aureus, Staphylococcus aureus* MRSA, *Staphylococcus epidermidis, Cutibacterium acnes*, or *Clostridium perfringens*. A composition, pharmaceutical composition, food additive, cosmetic composition, or hygiene product having an antimicrobial peptide variant including an amino acid sequence selected from SEQ ID NOs: 2-30 is also provided. The antimicrobial peptide can be an active ingredient in such compositions, additives, and products. A method of treating an infectious disease caused by bacteria is also provided. The method can include administering a pharmaceutical composition having the antimicrobial peptide as an active ingredient.

14 Claims, 1 Drawing Sheet
Specification includes a Sequence Listing.

FIG. 1

```
              10         20         30
Ple     GFGCNGPWDEDDMQCHNHCKSIKGYKGGYCAKGGFVCKCY
        ::::    :    :   ::  ::::::::::::   ::  :::::
Heg     GFGCT-IWGGNDKPCHRHCKSIKGYKGGYCKVGG-VCKCY
              10         20         30
```

Heg = Hegrisin = SEQ ID NO:1
Ple = Plectasin (control) = SEQ ID NO:32

FIG. 2

ANTIMICROBIAL PEPTIDE VARIANTS AND USES THEREOF

CROSS-REFERENCE TO RELATED APPLICATIONS

This application claims the benefit of priority under 35 U.S.C. § 119(e) of U.S. Provisional Application Ser. No. 62/925,485, filed on Oct. 24, 2019, the content of which is relied upon and incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 31, 2021, is named JMN-KLUO-0002NP_2_ST25.txt and is 13,239 bytes in size.

FIELD OF THE INVENTION

The disclosure relates generally to variants of an antimicrobial peptide derived from fungi, antimicrobial compositions containing the variants, and methods of using the same to treat or inhibit microbial infections in a subject.

BACKGROUND

Antimicrobial peptides are low-molecular-weight proteins that exhibit antimicrobial activity against bacteria, viruses, and fungi. Proteins of fungal origin have been identified as a rich source of antimicrobial peptides. Plectasin, isolated from the mushroom *Pseudoplectania nigrella*, is one example. Plectasin belongs to a class of antimicrobial peptides called defensins, which play a role in the body's defense against pathogens. Defensins are considered part of the innate immune response, and act mainly by disrupting the structure of bacterial cell membranes. Defensin-like peptides, such as plectasin, exhibit activity against several methicillin-resistant strains of *Staphylococcus aureus*.

SUMMARY

In various embodiments, an antimicrobial peptide variant consisting of an amino acid sequence selected from the group consisting of SEQ ID NOs: 2-30 is provided. The antimicrobial peptide variant can have antimicrobial activity against *Bacillus subtilis, Staphylococcus aureus, Staphylococcus aureus* MRSA, *Staphylococcus epidermidis, Cutibacterium acnes*, or *Clostridium perfringens*.

In various embodiments, a composition, pharmaceutical composition, food additive, cosmetic composition, or hygiene product comprising an antimicrobial peptide variant consisting of an amino acid sequence selected from the group consisting of SEQ ID NOs: 2-30 is provided. In some embodiments, the antimicrobial peptide can be an active ingredient.

In various embodiments, a method of treating an infectious disease caused by bacteria is provided. In some embodiments, the method can comprise administering a pharmaceutical composition comprising the antimicrobial peptide as an active ingredient.

Additional features and advantages will be set forth in the detailed description which follows, and in part will be readily apparent to those skilled in the art from that description or recognized by practicing the embodiments as described herein, including the detailed description which follows, the claims, as well as the appended drawings.

BRIEF DESCRIPTION OF THE FIGURES

The features and advantages of the antimicrobial peptide variants described herein will be more fully disclosed in, or rendered obvious by the following detailed description of the preferred embodiments, which are to be considered together with the accompanying drawings, wherein.

DETAILED DESCRIPTION

The antimicrobial peptide variants of the present disclosure are based on hegrisin, which is a peptide obtained from the genomic sequence of the fungi, *Helicocarpus griseus*. Hegrisin contains 38 amino acids, has a molecular weight of 4111.8 Da, and a +6.2 positive charge. Hegrisin and its variants have three pairs of disulfide bonds and an antiparallel β-sheet, which fold into a cysteine-stabilized alpha-beta (CSαβ) structure, similar to the structure of many vertebrate and fungal β-defensins.

In some embodiments, variants of hegrisin may consist of 20-100 amino acids. In some embodiments, the variants may consist of 30-50 or 35-45 amino acids or amino acid residues. All ranges are inclusive and combinable. In some embodiments, the hegrisin variants may consist of 38 amino acids or amino acid residues. In some embodiments, the hegrisin variants may comprise at least one amino acid sequence selected from the group consisting of SEQ ID NOs: 2-30.

In some embodiments, an amino group (—NH$_2$) or a methyl group (—CH$_3$) may be added to the C-terminal of the hegrisin variant. If the C-terminal of the hegrisin variant is amidated, resistance to proteases and positive net charge may be further enhanced. If the C-terminal is methylated, then in vivo stability may be increased based on an improved resistance to exopeptidases, which cleave the peptide from the terminal.

In some embodiments, the N-terminal of the hegrisin variants may be acetylated or palmitoylated. If the N-terminal is acetylated, superior antimicrobial activity may be achieved and the peptide may be protected from proteolytic degradation. If the N-terminal is palmitoylated, then permeability into cells may be enhanced.

In some embodiments, the hegrisin variants exhibit antimicrobial activity and may be commercially viable because they consist of short amino acid sequences. In addition, the hegrisin variants have strong inner membrane permeability. That is, the hegrisin variants likely exhibit antimicrobial activity by directly permeating into the inner membrane of bacteria. And, importantly, the hegrisin variants lack cytotoxicity and exhibit minimal or no hemolytic activity.

In some embodiments, the hegrisin variants of the present disclosure were designed and prepared to have antimicrobial activity against one or more pathogens selected from a group consisting of bacteria, such as Gram positive bacteria, Gram negative bacteria, etc., and fungi, such as yeast, molds, etc.

In some embodiments, the hegrisin variants have antimicrobial activity against one or more bacteria, including

*Escherichia coli, Staphylococcus aureus, Staphylococcus epidermidis, Streptococcus pneumoniae, Streptococcus pyogenes, Corynebacterium diphtheria, Corynebacterium jeikeium, Mycobacterium tuberculosis, Bacillus subtilis, Lactobacillus casei, Lactobacillus rhamnosus, Lactobacillus plantarum, Lactobacillus delbrueckii, Leuconostoc lactis, Streptococcus salivarius, Bifidobacterium longum, Cutibacterium acnes* and *Clostridium perfringens*.

In some embodiments, the hegrisin variants are formulated into an antimicrobial composition. In some embodiments, the composition is a pharmaceutical composition containing a hegrisin variant as an active ingredient. In some embodiments, a method for administering the composition to a subject in need thereof is provided. The method of administration is not particularly limited. In some embodiments, the composition may be administered intraarterially, intravenously, subcutaneously, intrarectally, intranasally, directly into muscle cells, or via any other parenteral route. In some embodiments, the composition may be administered orally (e.g., as a tablet, capsule, pill, suspension, liquid, etc.), nasally, rectally, transdermally, or via injection.

In some embodiments, the dosage of the composition will depend on the activity of the hegrisin variant, administration route, severity of the condition to be treated, condition and previous disease history of the patient, etc. However, starting with a lower dosage than is required to achieve the desired therapeutic effect and gradually increasing the dosage until the desired effect is achieved is within the knowledge of one skilled in the related art, and the specific administration dosage may be determined considering the age, sex, body type, and body weight. In some embodiments, the composition may be further processed before being formulated into a pharmaceutically acceptable pharmaceutical agent. For example, the composition may be pulverized or ground into particles. In some embodiments, depending on the desired effect, an effective dosage of the hegrisin variants may be about 0.1 to about 10 mg/kg, about 1 to about 2 mg/kg, about 0.5 to about 1 mg/kg, etc. In some embodiments, administration may be 1 to 10, 1 to 5, or 1 to 3 times a day. All ranges are inclusive and combinable.

In some embodiments, a pharmaceutical composition comprising a hegrisin variant may be prepared into a formulation of a single dosage form or a multiple dosage form using a pharmaceutically acceptable carrier and/or excipient according to a method typically employed by one of ordinary skill in the art. The formulation may be an oral formulation, such as a powder, granule, tablet, capsule, suspension, emulsion, syrup, aerosol, etc. The formulation may be formulated for external application such as an ointment, cream, etc., or any other pharmaceutical formulation such as a suppository, sterile solution for injection, etc. In some embodiments, the composition may further comprise a dispersant or stabilizer.

In some embodiments, the hegrisin variants exhibit antimicrobial activity against one or more microorganisms, including *Escherichia coli, Staphylococcus aureus, Staphylococcus epidermidis, Bacillus subtilis, Lactobacillus casei, Lactobacillus rhamnosus, Lactobacillus plantarum, Lactobacillus delbrueckii, Leuconostoc lactis, Streptococcus salivarius, Bifidobacterium longum, Cutibacterium acnes* and *Clostridium perfringens*. Accordingly, in some embodiments, the hegrisin variants may prevent or treat diseases caused by these or other bacteria, including but not limited to, respiratory infections, ear infections, sinusitis, tonsillitis, urinary tract infections, prostate infections, sexually transmitted infection, gastrointestinal infections, skin infections, food poisoning, candidiasis, typhoid, cholera, etc. Therefore, in some embodiments, the hegrisin variants may be used as an active ingredient in a pharmaceutical composition for preventing or treating an infectious disease caused by the microorganisms.

In some embodiments, the hegrisin variants may be used as an active ingredient in an antimicrobial cosmetic composition. The cosmetic composition may be in the form of a solution, powder, emulsion, lotion, spray, ointment, aerosol, cream, or foam. In some embodiments, the cosmetic composition may contain a carrier that is acceptable in a cosmetic formulation, additional active ingredients, or both. A "carrier that is acceptable in a cosmetic formulation" refers to a compound or composition already used in cosmetic formulations or a compound or composition to be developed, which lacks toxicity, instability, or irritability when applied to the skin of a subject. Examples of additional active ingredients include, but are not limited to steroids, salicylic acid, benzoyl peroxide, retinol, vitamin C, vitamin E, alpha hydroxy acids, dimethicone, and petrolatum.

As used herein, the term "skin" includes not only the face, but also the scalp and the entire body. For example, the cosmetic composition may be prepared as a shampoo, rinse, treatment, hair restorer, etc., for application to the scalp. And, for application to the entire body, the composition may be prepared as a body cleanser, soap, etc.

In some embodiments, the carrier may be contained in an amount of about 1 to about 99.99 wt %, or about 90 to about 99.99 wt %, based on the total weight of the cosmetic composition. For example, in some embodiments, the carrier may include an alcohol, oil, surfactant, fatty acid, silicone oil, humectant, moisturizer, viscosity modifier, emulsifier, stabilizer, sunscreen, UV absorbent, colorant, and/or fragrance, etc.

In some embodiments, the cosmetic composition may further comprise glycerin, butylene glycol, propylene glycol, polyoxyethylene hydrogenated castor oil, ethanol, triethanolamine, etc. In some embodiments, the composition may contain a trace amount of an antiseptic, fragrance, colorant, purified water, etc.

In some embodiments, the hegrisin variants may be used as an active ingredient of a hygiene product such as a wet wipe, hand sanitizer, mouthwash, oral antiseptic, toothpaste additive, etc. The hegrisin variants should be used in an amount that is effective for inhibiting microbial growth.

In some embodiments, the hegrisin variants may be used for cleaning, disinfecting or inhibiting microbial growth on any surface. Examples of surfaces, which may be contacted with the hegrisin variants include the surface(s) of manufacturing plants or equipment used therein, e.g., dairies, chemical or pharmaceutical process plants, water sanitation systems, oil processing plants, food processing plants, paper pulp processing plants, water treatment plants, and cooling towers. The hegrisin variants should be used in an amount that is effective for cleaning, disinfecting, or inhibiting microbial growth on the surface.

In some embodiments, the hegrisin variants may also be used as an active ingredient of an antimicrobial food. In such embodiments, the hegrisin variants can be used in an antimicrobial food or feed additive because the hegrisin variants have superior antimicrobial activity against Gram negative and Gram positive bacteria, as well as fungi.

In such embodiments, the type of food is not particularly limited. Examples of the food to which the substance can be added include a drink or beverage, including an alcoholic beverage, meat, sausage, bread, biscuit, rice cake, chocolate, candy, snack, pizza, noodles, gum, soup, a diary product, such as yogurt or ice cream, etc. etc. In some embodiments, the food is a vitamin supplement and other health-functional food. The hegrisin variants may be added to a food as is or mixed together with other food ingredients. The adequate amount of the active ingredient may be determined depending on the purpose of use (e.g., for prevention or treatment). In some embodiments, the hegrisin variants may be added in an amount of about 0.01 to about 50 wt. %, or about 0.1 to about 20 wt. %, or about 0.1 to about 10 wt. %, or about 0.1 to about 1 wt. %, based on the total weight of the food. All ranges are inclusive and combinable. In some embodiments, the amount of the active ingredient may be smaller than the above-described range. For example, a smaller amount may be used when the composition is used for health or hygiene or otherwise used for a long period of time. In some embodiments, a larger amount of the active ingredient may be used. For example, when there are no safety concerns.

In some embodiments, the hegrisin variants may be used as an active ingredient of an antimicrobial feed additive or feed composition, including any compound, preparation, mixture, or composition suitable for, or intended for intake by an animal such as a chicken, turkey, pig or swine, cow, sheep, horse, etc. In such embodiments, the hegrisin variants have provide antimicrobial activity against Gram positive and Gram negative bacteria. In some embodiments, the hegrisin variants may be added in an amount, including, e.g., about 0.01 to about 10.0%; about 0.05 to about 5.0%; or about 0.1 to about 1.0% (% meaning gram additive per 100 grams of feed). All ranges are inclusive and combinable.

In some embodiments, the hegrisin variants may also be used to preserve or hygienize antimicrobial feed because the hegrisin variants have superior antimicrobial activity against many bacteria such as *Clostridium perfringens*, a major feed-borne pathogen. The hegrisin variants can be added directly to the animal feed in a treatment process of feed at levels of 0.01 to 10.0%; more particularly 0.05 to 5.0%; or 0.1 to 1.0% (% meaning gram additive per 100 grams of hygiene). All ranges are inclusive and combinable.

In some embodiments, the hegrisin variants may be used as an active ingredient of a hygiene product such as a wet wipe, hand sanitizer, mouthwash, oral antiseptic, toothpaste additive, etc.

EXAMPLES

Strains, Reagents, Plasmids, Enzymes, and Growth Media

The following chemicals were purchased from Sigma-Aldrich Co. (St. Louis, USA) or Thermo Fisher Scientific Inc. (Pittsburgh, USA): peptone and yeast extract, Difc tryptic soy agar (TSA) and tryptic soy broth (TSB) (pancreatic digest of casein 15 g/L, papaic digest of Soybean 5 g/L, sodium chloride 5 g/L, Agar 15 g/L), Lysogeny (LB) broth (Luria low salt), Mueller Hinton broth (MH) (beef extract 2 g/L, acid digest of casein 17.5 g/L, starch 1.5 g/L), Reinforced Clostridial Medium (RCM). Restriction enzymes, Phusion high-fidelity DNA polymerase, and T4 ligase were purchased from New England Biolabs (Ipswich, USA). *Escherichia coli* DH5a, *P. pastoris* X33 and vectors pCR-blunt and pPicZalpha were purchased from Invitrogen (San Diego, Calif.). Minimal dextrose (MD) medium, minimal methanol (MM) medium, buffered glycerol complex (BMGY) medium, buffered methanol complex (BMMY) medium, and fermentation Basal Salts medium (BSM) were prepared according to the manual of *Pichia* Expression kit (Life Technologies Corp. USA).

The bacterial strains, including *Escherichia coli* ATCC 25922, *Staphylococcus aureus* ATCC 6538, *Staphylococcus aureus* MRSA ATCC 43300, *Staphylococcus epidermidis* ATCC 14990, *Bacillus subtilis* ATCC 6633, *Lactobacillus casei* ATCC 393, *Lactobacillus rhamnosus* ATCC 14957, *Lactobacillus plantarum* ATCC 14917, *Lactobacillus delbrueckii* ATCC 9649, *Leuconostoc lactis* ATCC 19256, *Streptococcus salivarius* ATCC 19258, *Bifidobacterium longum* ATCC 15707, *Cutibacterium acnes* ATCC 11827 and *Clostridium perfringens* ATCC 13124, were purchased from ATCC (Manassas, Va., USA).

Construction of Expression Plasmids

The hegrisin and hegrisin variants were developed according to codon usage bias and guanine-cytosine (GC) content of *P. pastoris* using Genscript's OptimumGen designing tool (Piscataway, N.J.). The designed hegrisin and variants were synthesized by Eton Bioscience (Boston, USA) and subcloned into pPicZalpha vector (Life Technologies Corp. USA). The resulting expression plasmid pPicZa was confirmed by restriction digestion and DNA sequencing (Eton Bioscience, USA).

Yeast Transformation and Screening of Recombinant *Pichia* Strains

The plasmid pPicZa was linearized with Pme I restriction enzyme from Thermo Scientific and then transformed into *P. pastoris* X33 by electroporation according to the manufacturer's instructions (Life Technologies Corp., USA). Transformants were screened on yeast extract peptone dextrose (YPD) (1% yeast extract, 2% peptone, 2% glucose) plates containing 100 ug/ml Zerocin (Life Technologies Corp., USA). The positive recombinants were analyzed by genomic polymerase chain reaction (PCR) with 5' AOX and 3' AOX primers. The recombinants identified by PCR were further screened in 125 mL shaken flasks. These strains were inoculated into 5 mL buffered glycerol complex medium (BMGY) (1% yeast extract, 2% peptone, 1.34% yeast nitrogen broth (YNB), $4 \times 10^{-5}$% biotin, 1% glycerol and 100 mM potassium phosphate, pH 6.0) and cultured for 24 hours at 30° C. in 50 mL shaker flasks in a shaking incubator (250 rpm). After culture reaches an OD600=6, 1 mL of culture was transferred to a 125 mL shaker flask containing 10 mL buffered methanol-complex medium (BMMY) (1% yeast extract, 2% peptone, 1.34% YNB, $4 \times 10^{-5}$% biotin, 0.5% methanol and 100 mM potassium phosphate, pH 6.0) and cultured for 24 hours at 30° C. (250 rpm). The enzyme expression was induced by adding 100% methanol to a final concentration of 0.5% methanol. The supernatant was collected by centrifugation at 12,000 rpm for 10 min (at 4° C.) for antimicrobial activity assay. The expressed peptides were analyzed by Tricine-SDS-PAGE.

Purification of Expressed Peptides

The fermentation supernatant was precipitated with 40-45% ammonium sulfate. The precipitated peptides were centrifuged at 15000×g for 30 min. The pellets were re-suspended with deionized water and purified using a Sephadex G-25 column and eluted with deionized water at a rate of 0.5 ml/min. The peak absorbance fractions were pooled for subsequent antimicrobial assays.

Antimicrobial Activity Assay

The antimicrobial activity of purified hegrisin and hegrisin variants were analyzed using an inhibition zone assay. Test strains of *S. aureus* ATCC 6538 were grown to OD600=0.5 at 37° C. in tryptic soy broth (TSB). A total of 100 μL of the cell suspension was inoculated into 20 ml of preheated trypticase soy agar (TSA) medium (at about 42° C.) containing 1.5% agar. The medium was rapidly mixed and poured into the Petri dish (100 mm). Then, 5 mm holes were punched into the agar media plate with a glass capillary and 50 μL samples of solution containing 10 μg hegrisin or hegrisin variants were dropped into the holes. Ampicillin (1

μg) was used as a positive control and sterile phosphate-buffered saline (PBS) was used a negative control. After incubation at 37° C. for 16-18 hours, the zones of growth inhibition were measured.

The Minimal Inhibitory Concentration (MIC) Assay

Minimal inhibitory concentration assays (MIC, expressed as μl/mL) against different microorganisms were performed according to the protocol described in the CLSI: (Methods for Dilution Antimicrobial Susceptibility Testing for Bacteria; Approved Standard—Eleventh Edition (2012). The tested bacteria *S. aureus* ATCC 6538; *S. aureus* MRSA ATCC 43300; *S. epidermidis* ATCC 14990; *B. subtilis* ATCC 6633, *L. casei* ATCC 393, *L. lactis* ATCC 19256; *L. rhamnosus* ATCC 14957; *L. plantarum* ATCC 14917; *L. delbrueckii* ATCC 9649; *S. salivarius* ATCC 19258; *B. longum* ATCC 15707; *C. acnes* ATCC 11827; and *C. perfringens* ATCC 13124 were grown to OD600=0.5 at 37° C. in Mueller-Hinton Broth (MHB) or Robertson's Cooked Meat (RCM) broth. The bacterial cultures were diluted with medium to $10^4$-$10^6$ CFU/mL. Then, 10 μL peptide solutions of various concentrations were added to 90 μL diluted culture fluid containing testing strains, resulting in a total volume of 100 μL. The 96-well microplates were incubated at 37° C. for 16 hours, and absorbance at 600 nm were taken to determine MIC. The MIC value was defined as the lowest peptide concentration that completely prevented growth using a microtiter optical plate reader.

Hemolytic Assay

For the hemolysis assays, human erythrocytes were obtained from healthy donors, washed 3 times using sterilized PBS and re-suspended to a concentration of 2% (v/v) with PBS. The hegrisin, HCN2016-01 peptide, and plectasin (control) were diluted to concentrations of 500, 250, 125, 62.5, 32, 16, 8, 4, 2, 1, and 0.5 μg/ml. A 100 μL solution of each peptide and a 100 μL suspension of red blood cells were mixed and added to the wells of a 96-well plate. PBS was used as negative control and Triton X-100 was used as a positive control.

The samples were incubated at 37° C. for 60 minutes and gently stirred during the incubation period. Then, the samples were centrifuged at 2000 rpm for 5 minutes. A total of 100 μL of the supernatant in each well was transferred to a new 96-well plate and absorbance was measured at 490 nm using a microplate reader (Molecular Devices, USA).

Example 1. Hegrisin Variants

Figure 1:
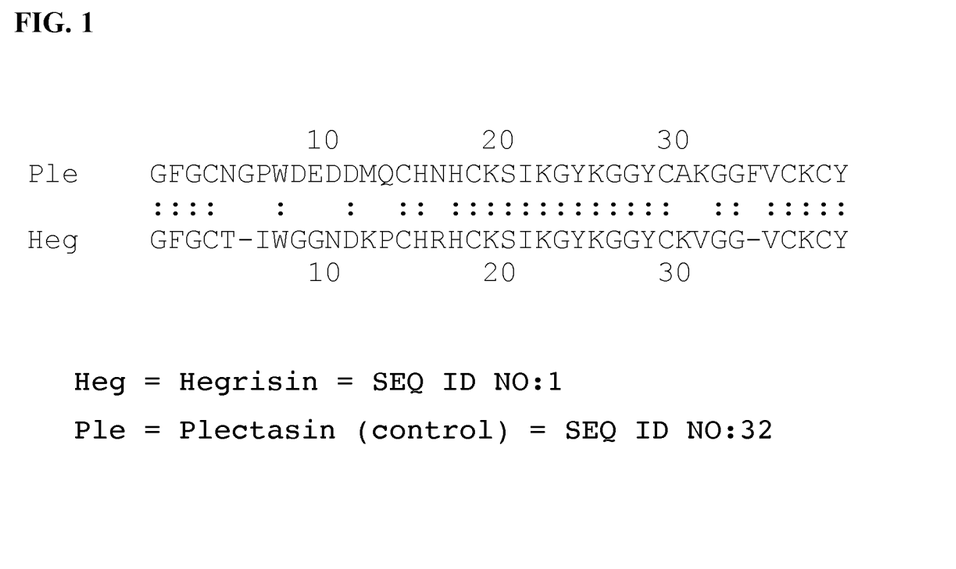
FIG. 1 shows the sequence alignment between plectasin (SEQ ID NO: 32) and hegrisin (SEQ ID NO: 1). The conserved portions of the sequences are indicated with dotted lines.

Hegrisin is a defensin-like antimicrobial peptide consisting of 38 amino acids and having a molecular weight of 4111.8 Da. After evaluation, it was determined that hegrisin has a cysteine-stabilized alpha-beta (CSαβ) structure similar to plectasin. FIG. 1 illustrates the alignment between the amino acid sequences of plectasin and hegrisin, where the conserved portions of the sequences are indicated with vertically oriented dots.

Thirty (30) hegrisin variants were designed based on their 3-D structure to determine if the antimicrobial activity of hegrisin could be improved. The amino acid sequences of hegrisin, the designed hegrisin variants, and plectasin are shown in Table 1.

TABLE 1

| SEQ ID NO: | Peptide | Sequence | Activity |
|---|---|---|---|
| 1 | Hegrisin | GFGCTIWGGNDKPCHRHCKSIKGYKGGYCKVGGVCKCY | 1 |
| 2 | HCN2016-01 | GWSCNIWNGNDEPCHQHCKSIRGYRGGYCKFGGICKCY | 2 |
| 3 | HCN2016-02 | GWSCNIWGGNDEPCHQHCKSIRGYRGGYCKFGGICKCY | 2 |
| 4 | HCN2016-03 | GFGCTIFGGNDKPCHRHCKSIKGYKGGYCKVGGVCKCY | 2 |
| 5 | HCN2016-04 | GWSCGFFGGNDEPCHQHCKSIRGYRGGYCKLGGICKCY | 2 |
| 6 | HCN2016-05 | GWGCGFFGGNDEPCHQHCKSIRGYRGGYCKFGGICKCY | 2 |
| 7 | HCN2016-06 | GFGCTIWGGNDKPCHRHCKSIRGYKGGYCKVGGVCECY | 1 |
| 8 | HCN2016-07 | GFGCTIWGGNDKPCHRHCKSIRGYKGGYCKVGGVCKCY | 1 |
| 9 | HCN2016-08 | GWSCNIFGGNDEPCHQHCKSIRGYRGGYCKFGGICKCY | 1 |
| 10 | HCN2016-09 | GFGCTIWGGNDEPCHQHCKSIRGYRGGYCKFGGICKCY | 2 |
| 11 | HCN2016-10 | GFGCNIFGGNDEPCHQHCKSIRGYRGGYCKFGGICKCY | 1 |
| 12 | HCN2016-11 | GFGCNIFGGNDKPCHRHCKSIKGYKGGYCKVGGVCKCY | 1 |
| 13 | HCN2016-12 | GFGCTIWGGNDRPCHRHCKSIKGYKGGYCKVGGVCKCY | 2 |
| 14 | HCN2016-13 | GFGCTIWGGNDRPCHNHCKSIKGYKGGYCKVGGVCKCY | 2 |
| 15 | HCN2016-14 | GWGCTIFGGNDKPCHRHCKSIKGYKGGYCKFGGICKCY | 1 |
| 16 | HCN2016-15 | GFGCTIWGGNDRPCHRHCKSIKGYKGGYCKIGGVCKCY | 1 |
| 17 | HCN2016-16 | GFGCTIWGGNDKPCHRHCKSIKGYKGGYCKIGGVCKCY | 2 |
| 18 | HCN2016-17 | GFGCGFFGGNDEPCHNHCKSIKGYRGGYCKFGGVCKCY | 2 |
| 19 | HCN2016-18 | GFGCGFFGGNDEPCHNHCKSIKGYKGGYCAKGGVCKCY | 1 |
| 20 | HCN2016-19 | GFGCGFFGGNDEPCHQHCKSIRGYRGGYCKFGGICKCY | 2 |

TABLE 1-continued

| SEQ ID NO: | Peptide | Sequence | Activity |
|---|---|---|---|
| 21 | HCN2016-20 | GFGCGFFGGNDQPCHQHCKSIRGYRGGYCKFGGICKCY | 2 |
| 22 | HCN2016-21 | GFGCGFFGGNDLRCHQHCKSIRGYRGGYCKFGGICKCY | 1 |
| 23 | HCN2016-22 | GFGCGFFGGNDKPCHQHCKSIRGYRGGYCKFGGICKCY | 1 |
| 24 | HCN2016-23 | GWSCGFFGGNDQPCHQHCKSIRGYRGGYCKFGGICKCY | 1 |
| 25 | HCN2016-24 | GWSCGFFGGNDEPCKQHCKSIRGYRGGYCKFGGICKCY | 1 |
| 26 | HCN2016-25 | GWSCGFFGGNDEPCHNHCKSIRGYRGGYCKFGGICKCY | 1 |
| 27 | HCN2016-26 | GWSCGFFGGNDEPCHNHCKSIKGYRGGYCKFGGVCKCY | 1 |
| 28 | HCN2016-27 | GWSCGFFGGNDEPCHQKCKSIRGYRGGYCKFGGICKCY | 2 |
| 29 | HCN2016-28 | GWSCGFFGGNDEPCHRHCKSIRGYRGGYCKFGGICKCY | 1 |
| 30 | HCN2016-29 | GWSCGFFGGNDKPCHRHCKSIKGYKGGYCKVGGVCKCY | 2 |
| 31 | HCN2016-30 | GWSCGFFGGNDYRCHRHCKSIKGYKGGYCKLGGICKCY | 1 |

Example 2. Evaluation of Antimicrobial Activity

The hegrisin and hegrisin variants were expressed in *P. pastoris* X33. The supernatant was collected by centrifugation at 12,000 rpm for 10 minutes (at 4° C.). The fermentation supernatant was precipitated with 40-45% ammonium sulfate. The precipitated peptides were centrifuged at 15,000×g for 30 min. The pellets were re-suspended with deionized water and purified with Sephadex G-25 columns.

The antimicrobial activity of purified hegrisin and hegrisin variants were analyzed using an inhibition zone assay. Test strains of *S. aureus* ATCC 6538 were grown to OD600=0.5 at 37° C. in TSB broth. A total of 100 μL of the cell suspension was inoculated into 20 ml of preheated TSA agar medium (at about 42° C.) containing 1.5% agar. The medium was rapidly mixed and poured into a Petri dish (100 mm). Then, 5 mm holes were punched into the agar media plate with a glass capillary and 50 μL samples of solution containing 10 μg hegrisin or hegrisin variants were dropped into the holes. Ampicillin (1 μg) was used as a positive control and sterile PBS was used a negative control. After incubation at 37° C. for 16-18 hours, the zones of growth inhibition were measured.

The hegrisin variants and corresponding antimicrobial activities, relative to the activity of unmodified hegrisin, are shown in Table 1. An activity value of 1 corresponds to an activity correlating to that of hegrisin. An activity value of 2 corresponds to an activity that is better than that of hegrisin.

Example 3. Measuring Minimal Inhibitory Concentration

Five hegrisin variants (SEQ ID NOs: 2-6) with particularly good antimicrobial activity were selected for testing using a minimal inhibitory concentration assay (MIC, expressed as μl/mL) against different microorganisms following the protocol described in the CLSI: Methods for Dilution Antimicrobial Susceptibility Testing for Bacteria; Approved Standard—Eleventh Edition (2012).

Compared to wild type hegrisin (SEQ ID NO: 1), hegrisin variants HCN2016-01 (SEQ ID NO: 2), HCN2016-02 (SEQ ID NO: 3), HCN2016-03 (SEQ ID NO: 4), HCN2016-04 (SEQ ID NO: 5) and HCN2016-05 (SEQ ID NO: 6) exhibited improved antimicrobial activity (i.e., lower MIC values) against the bacteria *S. aureus* ATCC 6538. Compared to wild type hegrisin (SEQ ID NO: 1), hegrisin variants HCN2016-01 (SEQ ID NO: 2), HCN2016-03 (SEQ ID NO: 4), and HCN2016-04 (SEQ ID NO: 5) had an improved antimicrobial activity against the bacteria *S. aureus* MRSA ATCC 43300. And, compared to wild type hegrisin (SEQ ID NO: 1), hegrisin variants HCN2016-01 (SEQ ID NO: 2) and HCN2016-04 (SEQ ID NO: 5) exhibited improved antimicrobial activity against the bacteria *S. epidermidis* ATCC 14990. The minimal inhibitory concentration (MIC) of hegrisin and variants against Gram-positive bacteria are shown in Table 2.

TABLE 2

Minimal inhibitory concentration (MIC) (μg/ml)

| Microbe | SEQ ID NO: | | | | | |
|---|---|---|---|---|---|---|
| | 1 | 2 | 3 | 4 | 5 | 6 |
| *S. aureus* ATCC 6538 | 1.67 | 0.30 | 1.40 | 1.33 | 0.40 | 1.44 |
| *S. aureus* MRSA ATCC 43300 | 1.34 | 0.73 | 2.80 | 0.81 | 0.86 | 2.88 |
| *S. epidermidis* ATCC 14990 | 0.38 | 0.31 | 1.40 | 1.30 | 0.33 | 2.80 |

Example 4. Evaluation of Antimicrobial Activity of HCN2016-01 Peptide

The hegrisin variant HCN2016-01 (SEQ ID NO: 2) had particularly good antimicrobial activity and was selected for further analysis. The minimal inhibitory concentration (MIC) was determined to test for its antimicrobial activity following the CLSI guidelines. The HCN2016-01 peptide (SEQ ID NO: 2) was tested against the following bacteria: *S. aureus* ATCC 6538; *S. aureus* MRSA ATCC 43300; *S. epidermidis* ATCC 14990; *B. subtilis* ATCC 6633; *L. casei* ATCC 393; *L. lactis* ATCC 19256; *L. rhamnosus* ATCC 14957; *L. plantarum* ATCC 14917; *L. delbrueckii* ATCC 9649; *S. salivarius* ATCC 19258; *B. longum* ATCC 15707; *C. acnes* ATCC 11827; and *C. perfringens* ATCC 13124.

The HCN2016-01 peptide (SEQ ID NO: 2) exhibited strong activity against Gram positive bacteria *S. aureus* ATCC 6538; *S. aureus* MRSA ATCC 43300; *S. epidermidis* ATCC 14990; *B. subtilis* ATCC 6633; *L. casei* ATCC 393; *L. delbrueckii* ATCC 9649; *S. salivarius* ATCC 19258; *B. longum* ATCC 15707; *C. acnes* ATCC 11827; and *C. perfringens* ATCC 13124, but minimal or no activity against *L. casei* ATCC 393 and Gram negative bacteria *E. coli* 25923. The minimal inhibitory concentration (MIC) of the HCN2016-01 peptide (SEQ ID NO: 2) against the bacteria are shown in Table 3.

TABLE 3

Minimal inhibitory concentration (MIC) (µg/ml)

| Microbe | HCN2016-01 (SEQ ID NO: 2) |
|---|---|
| *S. aureus* ATCC 6538 | 0.30 |
| *S. aureus* MRSA ATCC 43300 | 0.73 |
| *S. epidermidis* ATCC 14990 | 0.31 |
| *B. subtilis* ATCC 6633 | 0.50 |
| *L. lactis* ATCC 19256 | 0.50 |
| *L. rhamnosus* ATCC 14957 | 32.0 |
| *L. plantarum* ATCC 14917 | 16.0 |
| *L. delbrueckii* ATCC 9649 | 8.0 |
| *S. salivarius* ATCC 19258 | 4.0 |
| *B. longum* ATCC 15707 | 8.0 |
| *C. acnes* ATCC 11827 | 8.0 |
| *C. perfringens* ATCC 13124 | 6.81 |
| *L. casei* ATCC 393 | >500.0 |
| *E. coli* ATCC 25922 | >500.0 |

Example 5. Hemolytic Activity of HCN2016-01 Peptide

For hemolysis assays, human erythrocytes were obtained from healthy donors, washed 3 times using sterilized PBS, and re-suspended to a concentration of 2% (v/v) with PBS. The HCN2016-01 peptide (SEQ ID NO: 2) and plectasin (control) were diluted to concentrations of 500; 250; 125; 62.5; 32; 16; 8; 4; 2; 1; and 0.5 µg/ml. A 100 µL of each peptide solution was mixed with a 100 µL solution of a red blood cell suspension and added to separate wells of a 96-well plate. PBS was used as negative control and Triton X-100 was used as a positive control. The samples were incubated at 37° C. for 60 minutes and gently stirred during the incubation period. The samples were then centrifuged at 2000 rpm for 5 minutes. A total of 100 µL of the supernatant in each well was transferred to a new 96-well plate and absorbance was measured at 490 nm using a microplate reader (Molecular Devices, USA).

Figure 2:
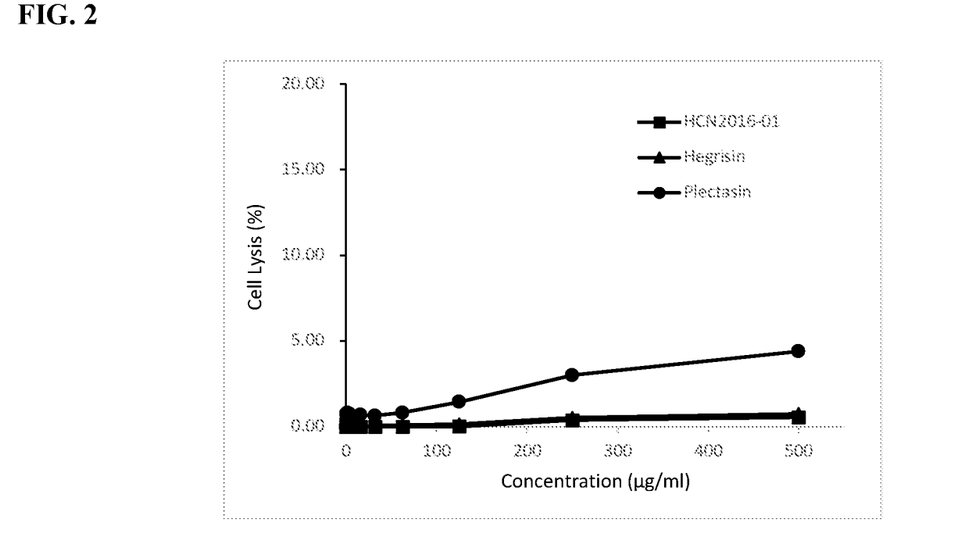
FIG. 2 shows the cell lysis observed for various concentrations of plectasin, hegrisin, and a hegrisin variant (HCN2016-01).

As shown in FIG. 2, hegrisin and the HCN2016-01 peptide (SEQ ID NO: 2) exhibited no significant lysis at any concentration of peptides tested (0.5-500 µg/ml). By contrast, plectasin exhibited lysis at nearly all concentrations, and the cell lysis increased significantly as the concentration was increased from 62.5 µg/ml to 500 µg/ml.

As described above, the HCN2016-01 peptide exhibited remarkable antibacterial effects against gram-positive bacteria and was not harmful to human cells. Accordingly, the HCN2016-01 peptide (SEQ ID NO: 2) and other hegrisin variants described herein are expected to be effective active ingredients for feed additives, food preservatives, cosmetics, and/or pharmaceutical compositions.

The foregoing is provided for purposes of illustrating, explaining, and describing embodiments of the invention. Modifications and adaptations to these embodiments will be apparent to those skilled in the art and may be made without departing from the scope or spirit of the invention.

Although the subject matter has been described in terms of exemplary embodiments, it is not limited thereto. Rather, the appended claims should be construed broadly, to include other variants and embodiments, which may be made by those skilled in the art.

The invention claimed is:

1. An antimicrobial peptide variant consisting of an amino acid sequence selected from the group consisting of SEQ ID NOs: 2-30.

2. The antimicrobial peptide variant according to claim 1, wherein the antimicrobial peptide variant has antimicrobial activity against Gram-positive bacteria.

3. The antimicrobial peptide variant according to claim 2, wherein the Gram-positive bacteria is *Staphylococcus aureus*.

4. The antimicrobial peptide variant according to claim 2, wherein the Gram-positive bacteria is *Staphylococcus aureus* MRSA.

5. The antimicrobial peptide variant according to claim 2, wherein the Gram-positive bacteria is *Staphylococcus epidermidis*.

6. The antimicrobial peptide variant according to claim 1, wherein the amino acid sequence is SEQ ID NO: 2.

7. The antimicrobial peptide variant according to claim 6, wherein the antimicrobial peptide variant has antimicrobial activity against *Bacillus subtilis*, *Staphylococcus aureus*, *Staphylococcus aureus* MRSA, *Staphylococcus epidermidis*, *Cutibacterium acnes*, or *Clostridium perfringens*.

8. An antimicrobial peptide composition comprising the antimicrobial peptide of claim 1 as an active ingredient.

9. A pharmaceutical composition comprising the antimicrobial peptide of claim 1 as an active ingredient.

10. An antimicrobial food additive comprising the antimicrobial peptide of claim 1 as an active ingredient.

11. A cosmetic composition comprising the antimicrobial peptide of claim 1 as an active ingredient.

12. A hygiene product comprising the antimicrobial peptide of claim 1 as an active ingredient.

13. A method of treating an infectious disease caused by bacteria comprising administering a pharmaceutical composition comprising the antimicrobial peptide of claim 1 as an active ingredient.

14. The method according to claim 13, wherein the antimicrobial peptide, wherein the amino acid sequence is SEQ ID NO: 2.

* * * * *

SEQUENCE LISTING

<160> NUMBER OF SEQ ID NOS: 32

<210> SEQ ID NO 1
<211> LENGTH: 38
<212> TYPE: PRT
<213> ORGANISM: HELICOCARPUS GRISEUS

<400> SEQUENCE: 1

Gly Phe Gly Cys Thr Ile Trp Gly Gly Asn Asp Lys Pro Cys His Arg
1               5                   10                  15

His Cys Lys Ser Ile Lys Gly Tyr Lys Gly Gly Tyr Cys Lys Val Gly
            20                  25                  30

Gly Val Cys Lys Cys Tyr
        35

<210> SEQ ID NO 2
<211> LENGTH: 38
<212> TYPE: PRT
<213> ORGANISM: HELICOCARPUS GRISEUS

<400> SEQUENCE: 2

Gly Trp Ser Cys Asn Ile Trp Asn Gly Asn Asp Glu Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 3
<211> LENGTH: 38
<212> TYPE: PRT
<213> ORGANISM: HELICOCARPUS GRISEUS

<400> SEQUENCE: 3

Gly Trp Ser Cys Asn Ile Trp Gly Gly Asn Asp Glu Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 4
<211> LENGTH: 38
<212> TYPE: PRT
<213> ORGANISM: HELICOCARPUS GRISEUS

<400> SEQUENCE: 4

Gly Phe Gly Cys Thr Ile Phe Gly Gly Asn Asp Lys Pro Cys His Arg
1               5                   10                  15

His Cys Lys Ser Ile Lys Gly Tyr Lys Gly Gly Tyr Cys Lys Val Gly
            20                  25                  30

Gly Val Cys Lys Cys Tyr
        35

<210> SEQ ID NO 5
<211> LENGTH: 38
<212> TYPE: PRT
<213> ORGANISM: HELICOCARPUS GRISEUS

<400> SEQUENCE: 5

Gly Trp Ser Cys Gly Phe Phe Gly Gly Asn Asp Glu Pro Cys His Gln
1               5                   10                  15

His Cys Lys Ser Ile Arg Gly Tyr Arg Gly Gly Tyr Cys Lys Leu Gly
            20                  25                  30

Gly Ile Cys Lys Cys Tyr
        35

<210> SEQ ID NO 6
<211> LENGTH: 38
<212> TYPE: PRT
<213> ORGANISM: HELICOCARPUS GRISEUS

<400> SEQUENCE: 6

Gly Trp Gly Cys Gly Phe Phe Gly Gly Asn Asp Glu Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 7
<211> LENGTH: 38
<212> TYPE: PRT

<213> ORGANISM: HELICOCARPUS GRISEUS

<400> SEQUENCE: 7

Gly Phe Gly Cys Thr Ile Trp Gly Gly Asn Asp Lys Pro Cys His Arg
1               5                   10                  15

His Cys Lys Ser Ile Arg Gly Tyr Lys Gly Gly Tyr Cys Lys Val Gly
            20                  25                  30

Gly Val Cys Glu Cys Tyr
        35

<210> SEQ ID NO 8
<211> LENGTH: 38
<212> TYPE: PRT
<213> ORGANISM: HELICOCARPUS GRISEUS

<400> SEQUENCE: 8

Gly Phe Gly Cys Thr Ile Trp Gly Gly Asn Asp Lys Pro Cys His Arg
1               5                   10                  15

His Cys Lys Ser Ile Arg Gly Tyr Lys Gly Gly Tyr Cys Lys Val Gly
            20                  25                  30

Gly Val Cys Lys Cys Tyr
        35

<210> SEQ ID NO 9
<211> LENGTH: 38
<212> TYPE: PRT
<213> ORGANISM: HELICOCARPUS GRISEUS

<400> SEQUENCE: 9

Gly Trp Ser Cys Asn Ile Phe Gly Gly Asn Asp Glu Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 10
<211> LENGTH: 38
<212> TYPE: PRT
<213> ORGANISM: HELICOCARPUS GRISEUS

<400> SEQUENCE: 10

Gly Phe Gly Cys Thr Ile Trp Gly Gly Asn Asp Glu Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 11
<211> LENGTH: 38
<212> TYPE: PRT
<213> ORGANISM: HELICOCARPUS GRISEUS

<400> SEQUENCE: 11

Gly Phe Gly Cys Asn Ile Phe Gly Gly Asn Asp Glu Pro Cys His Gln
1               5                   10                  15

His Cys Lys Ser Ile Arg Gly Tyr Arg Gly Gly Tyr Cys Lys Phe Gly
            20                  25                  30

```
Gly Ile Cys Lys Cys Tyr
        35

<210> SEQ ID NO 12
<211> LENGTH: 38
<212> TYPE: PRT
<213> ORGANISM: HELICOCARPUS GRISEUS

<400> SEQUENCE: 12

Gly Phe Gly Cys Asn Ile Phe Gly Gly Asn Asp Lys Pro Cys His Arg
1               5                   10                  15

His Cys Lys Ser Ile Lys Gly Tyr Lys Gly Gly Tyr Cys Lys Val Gly
            20                  25                  30

Gly Val Cys Lys Cys Tyr
        35

<210> SEQ ID NO 13
<211> LENGTH: 38
<212> TYPE: PRT
<213> ORGANISM: HELICOCARPUS GRISEUS

<400> SEQUENCE: 13

Gly Phe Gly Cys Thr Ile Trp Gly Gly Asn Asp Arg Pro Cys His Arg
1               5                   10                  15

His Cys Lys Ser Ile Lys Gly Tyr Lys Gly Gly Tyr Cys Lys Val Gly
            20                  25                  30

Gly Val Cys Lys Cys Tyr
        35

<210> SEQ ID NO 14
<211> LENGTH: 38
<212> TYPE: PRT
<213> ORGANISM: HELICOCARPUS GRISEUS

<400> SEQUENCE: 14

Gly Phe Gly Cys Thr Ile Trp Gly Gly Asn Asp Arg Pro Cys His Asn
1               5                   10                  15

His Cys Lys Ser Ile Lys Gly Tyr Lys Gly Gly Tyr Cys Lys Val Gly
            20                  25                  30

Gly Val Cys Lys Cys Tyr
        35

<210> SEQ ID NO 15
<211> LENGTH: 38
<212> TYPE: PRT
<213> ORGANISM: HELICOCARPUS GRISEUS

<400> SEQUENCE: 15

Gly Trp Gly Cys Thr Ile Phe Gly Gly Asn Asp Lys Pro Cys His Arg
1               5                   10                  15

His Cys Lys Ser Ile Lys Gly Tyr Lys Gly Gly Tyr Cys Lys Phe Gly
            20                  25                  30

Gly Ile Cys Lys Cys Tyr
        35

<210> SEQ ID NO 16
<211> LENGTH: 38
<212> TYPE: PRT
<213> ORGANISM: HELICOCARPUS GRISEUS
```

<400> SEQUENCE: 16

Gly Phe Gly Cys Thr Ile Trp Gly Gly Asn Asp Arg Pro Cys His Arg
1               5                   10                  15

His Cys Lys Ser Ile Lys Gly Tyr Lys Gly Gly Tyr Cys Lys Ile Gly
            20                  25                  30

Gly Val Cys Lys Cys Tyr
        35

<210> SEQ ID NO 17
<211> LENGTH: 38
<212> TYPE: PRT
<213> ORGANISM: HELICOCARPUS GRISEUS

<400> SEQUENCE: 17

Gly Phe Gly Cys Thr Ile Trp Gly Gly Asn Asp Lys Pro Cys His Arg
1               5                   10                  15

His Cys Lys Ser Ile Lys Gly Tyr Lys Gly Gly Tyr Cys Lys Ile Gly
            20                  25                  30

Gly Val Cys Lys Cys Tyr
        35

<210> SEQ ID NO 18
<211> LENGTH: 38
<212> TYPE: PRT
<213> ORGANISM: HELICOCARPUS GRISEUS

<400> SEQUENCE: 18

Gly Phe Gly Cys Gly Phe Phe Gly Gly Asn Asp Glu Pro Cys His Asn
1               5                   10                  15

His Cys Lys Ser Ile Lys Gly Tyr Arg Gly Gly Tyr Cys Lys Phe Gly
            20                  25                  30

Gly Val Cys Lys Cys Tyr
        35

<210> SEQ ID NO 19
<211> LENGTH: 38
<212> TYPE: PRT
<213> ORGANISM: HELICOCARPUS GRISEUS

<400> SEQUENCE: 19

Gly Phe Gly Cys Gly Phe Phe Gly Gly Asn Asp Glu Pro Cys His Asn
1               5                   10                  15

His Cys Lys Ser Ile Lys Gly Tyr Lys Gly Gly Tyr Cys Ala Lys Gly
            20                  25                  30

Gly Val Cys Lys Cys Tyr
        35

<210> SEQ ID NO 20
<211> LENGTH: 38
<212> TYPE: PRT
<213> ORGANISM: HELICOCARPUS GRISEUS

<400> SEQUENCE: 20

Gly Phe Gly Cys Gly Phe Phe Gly Gly Asn Asp Glu Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 21
<211> LENGTH: 38
<212> TYPE: PRT
<213> ORGANISM: HELICOCARPUS GRISEUS

<400> SEQUENCE: 21

Gly Phe Gly Cys Gly Phe Phe Gly Gly Asn Asp Gln Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 22
<211> LENGTH: 38
<212> TYPE: PRT
<213> ORGANISM: HELICOCARPUS GRISEUS

<400> SEQUENCE: 22

Gly Phe Gly Cys Gly Phe Phe Gly Gly Asn Asp Leu Arg Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 23
<211> LENGTH: 38
<212> TYPE: PRT
<213> ORGANISM: HELICOCARPUS GRISEUS

<400> SEQUENCE: 23

Gly Phe Gly Cys Gly Phe Phe Gly Gly Asn Asp Lys Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 24
<211> LENGTH: 38
<212> TYPE: PRT
<213> ORGANISM: HELICOCARPUS GRISEUS

<400> SEQUENCE: 24

Gly Trp Ser Cys Gly Phe Phe Gly Gly Asn Asp Gln Pro Cys His Gln
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 25
<211> LENGTH: 38
<212> TYPE: PRT
<213> ORGANISM: HELICOCARPUS GRISEUS

<400> SEQUENCE: 25

Gly Trp Ser Cys Gly Phe Phe Gly Gly Asn Asp Glu Pro Cys Lys Gln
1               5                   10                  15

```
His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 26
<211> LENGTH: 38
<212> TYPE: PRT
<213> ORGANISM: HELICOCARPUS GRISEUS

<400> SEQUENCE: 26

Gly Trp Ser Cys Gly Phe Phe Gly Gly Asn Asp Glu Pro Cys His Asn
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 27
<211> LENGTH: 38
<212> TYPE: PRT
<213> ORGANISM: HELICOCARPUS GRISEUS

<400> SEQUENCE: 27

Gly Trp Ser Cys Gly Phe Phe Gly Gly Asn Asp Glu Pro Cys His Asn
1               5                   10                  15

His Cys Lys Ser Ile Lys Gly Tyr Arg Gly Gly Tyr Cys Lys Phe Gly
            20                  25                  30

Gly Val Cys Lys Cys Tyr
        35

<210> SEQ ID NO 28
<211> LENGTH: 38
<212> TYPE: PRT
<213> ORGANISM: HELICOCARPUS GRISEUS

<400> SEQUENCE: 28

Gly Trp Ser Cys Gly Phe Phe Gly Gly Asn Asp Glu Pro Cys His Gln
1               5                   10                  15

Lys Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 29
<211> LENGTH: 38
<212> TYPE: PRT
<213> ORGANISM: HELICOCARPUS GRISEUS

<400> SEQUENCE: 29

Gly Trp Ser Cys Gly Phe Phe Gly Gly Asn Asp Glu Pro Cys His Arg
1               5                   10                  15

His Cys Lys Ser Ile Arg Gly Tyr Arg Gly Gly Tyr Cys Lys Phe Gly
            20                  25                  30

Gly Ile Cys Lys Cys Tyr
        35

<210> SEQ ID NO 30
<211> LENGTH: 38
<212> TYPE: PRT
```

```
<213> ORGANISM: HELICOCARPUS GRISEUS

<400> SEQUENCE: 30

Gly Trp Ser Cys Gly Phe Phe Gly Gly Asn Asp Lys Pro Cys His Arg
1               5                   10                  15

His Cys Lys Ser Ile Lys Gly Tyr Lys Gly Gly Tyr Cys Lys Val Gly
            20                  25                  30

Gly Val Cys Lys Cys Tyr
        35

<210> SEQ ID NO 31
<211> LENGTH: 38
<212> TYPE: PRT
<213> ORGANISM: HELICOCARPUS GRISEUS

<400> SEQUENCE: 31

Gly Trp Ser Cys Gly Phe Phe Gly Gly Asn Asp Tyr Arg Cys His Arg
1               5                   10                  15

His Cys Lys Ser Ile Lys Gly Tyr Lys Gly Gly Tyr Cys Lys Leu Gly
            20                  25                  30

Gly Ile Cys Lys Cys Tyr
        35

<210> SEQ ID NO 32
<211> LENGTH: 40
<212> TYPE: PRT
<213> ORGANISM: PLECTASIN

<400> SEQUENCE: 32

Gly Phe Gly Cys Asn Gly Pro Trp Asp Glu Asp Asp Met Gln Cys His
1               5                   10                  15

Asn His Cys Lys Ser Ile Lys Gly Tyr Lys Gly Gly Tyr Cys Ala Lys
            20                  25                  30

Gly Gly Phe Val Cys Lys Cys Tyr
        35                  40
```